United States Patent [19]
Rudie

[11] Patent Number: 6,032,078
[45] Date of Patent: Feb. 29, 2000

[54] VOLTAGE CONTROLLED VARIABLE TUNING ANTENNA

[75] Inventor: Eric N. Rudie, Maple Grove, Minn.

[73] Assignee: Urologix, Inc., Minneapolis, Minn.

[21] Appl. No.: 08/955,895

[22] Filed: Oct. 22, 1997

Related U.S. Application Data

[62] Division of application No. 08/621,634, Mar. 26, 1996, Pat. No. 5,938,692.

[51] Int. Cl.$^7$ ........................................................ A61F 2/00
[52] U.S. Cl. ........................... 607/101; 607/156; 607/105; 607/113; 607/116; 128/898
[58] Field of Search ..................................... 607/100–101, 607/115–116, 154, 156; 606/41–42, 45, 48–50; 604/20–21; 128/898

[56] References Cited

U.S. PATENT DOCUMENTS

| | | |
|---|---|---|
| 2,407,690 | 9/1946 | Southworth . |
| 3,411,507 | 11/1968 | Wingrove . |
| 3,494,723 | 2/1970 | Gray . |
| 4,140,130 | 2/1979 | Storm, III . |
| 4,154,246 | 5/1979 | LeVeen . |
| 4,162,500 | 7/1979 | Jacobi et al. . |
| 4,204,549 | 5/1980 | Paglione . |
| 4,285,346 | 8/1981 | Armitage . |
| 4,290,435 | 9/1981 | Waggott . |
| 4,311,154 | 1/1982 | Sterzer et al. . |
| 4,312,364 | 1/1982 | Convert et al. . |
| 4,375,220 | 3/1983 | Matvias . |
| 4,448,198 | 5/1984 | Turner . |
| 4,497,324 | 2/1985 | Sullivan et al. . |
| 4,557,272 | 12/1985 | Carr . |
| 4,559,951 | 12/1985 | Dahl et al. . |
| 4,583,556 | 4/1986 | Hines et al. . |
| 4,601,296 | 7/1986 | Yerushaimi . |
| 4,612,940 | 9/1986 | Kasevich et al. . |
| 4,632,127 | 12/1986 | Sterzer . |
| 4,643,186 | 2/1987 | Rosen et al. . |

(List continued on next page.)

FOREIGN PATENT DOCUMENTS

| | | |
|---|---|---|
| 0 048 402 | 3/1982 | European Pat. Off. . |
| 0 105 677 | 4/1984 | European Pat. Off. . |
| 0 246 176 | 11/1987 | European Pat. Off. . |
| 0 248 758 | 12/1987 | European Pat. Off. . |
| 0 253 677 | 1/1988 | European Pat. Off. . |
| 0 370 890 | 5/1990 | European Pat. Off. . |

(List continued on next page.)

OTHER PUBLICATIONS

Turner, Paul F., *Interstitial EM Applicator/Temperature Probes*, IEEE/Eight Annual Conference of the Engineering in Medicine and Biology Society, pp. 1454–1457.

(List continued on next page.)

Primary Examiner—Cary O'Connor
Assistant Examiner—Ryan Carter
Attorney, Agent, or Firm—Kinney & Lange, P.A.

[57] ABSTRACT

A catheter shaft carries a coaxial cable, the terminal end of which contains a dipole antenna with opposing first and second helical elements. The first and second helical elements originate from a common connection to an outer conductor of the coaxial cable. The first and second helical elements are formed by winding flat wire around an outer insulator of the coaxial cable near a terminal end of the coaxial cable. A variable, controllable impedance is connected between an inner conductor of the coaxial cable and a point on the second helical element where the resistive component of the antenna's impedance matches the characteristic impedance of the coaxial cable. The impedance match minimizes reflective losses of the antenna, thereby maximizing power transferred to the antenna. The antenna has an effective electrical length which is equal to one-half the wavelength of the radiation emitted, independent of the physical length of the antenna. The antenna also has a radiation length which can be adjusted by varying the number in pitch and turns of the flat wire and the location of the impedance matching point.

8 Claims, 8 Drawing Sheets

U.S. PATENT DOCUMENTS

| | | |
|---|---|---|
| 4,662,383 | 5/1987 | Sogawa et al. . |
| 4,669,475 | 6/1987 | Turner . |
| 4,676,258 | 6/1987 | Inokuchi et al. . |
| 4,690,156 | 9/1987 | Kikuchi et al. . |
| 4,700,716 | 10/1987 | Kasevich et al. . |
| 4,712,559 | 12/1987 | Turner . |
| 4,732,161 | 3/1988 | Azam et al. . |
| 4,776,086 | 10/1988 | Kasevich et al. . |
| 4,798,215 | 1/1989 | Turner . |
| 4,800,899 | 1/1989 | Elliott . |
| 4,813,429 | 3/1989 | Eshel et al. . |
| 4,821,725 | 4/1989 | Azam et al. . |
| 4,823,812 | 4/1989 | Eshel et al. . |
| 4,825,880 | 5/1989 | Stauffer et al. . |
| 4,841,988 | 6/1989 | Fetter et al. . |
| 4,860,752 | 8/1989 | Turner . |
| 4,865,047 | 9/1989 | Chou et al. . |
| 4,872,458 | 10/1989 | Kanehira et al. ................... 128/401 |
| 4,924,863 | 5/1990 | Sterzer . |
| 4,932,420 | 6/1990 | Goldstein . |
| 4,934,365 | 6/1990 | Morgenthaler ...................... 607/101 |
| 4,945,318 | 7/1990 | Kabachinski . |
| 4,955,377 | 9/1990 | Lennox et al. . |
| 4,967,765 | 11/1990 | Turner et al. . |
| 4,993,430 | 2/1991 | Shimoyama et al. . |
| 4,998,933 | 3/1991 | Eggers et al. . |
| 5,003,991 | 4/1991 | Takayama et al. . |
| 5,007,437 | 4/1991 | Sterzer . |
| 5,026,959 | 6/1991 | Ito et al. . |
| 5,056,531 | 10/1991 | Shimoyama . |
| 5,057,106 | 10/1991 | Kasevich et al. . |
| 5,061,267 | 10/1991 | Zeiher . |
| 5,097,845 | 3/1992 | Fetter et al. . |
| 5,106,360 | 4/1992 | Ishiwara et al. . |
| 5,151,100 | 9/1992 | Abele et al. . |
| 5,213,097 | 5/1993 | Zeindler . |
| 5,234,004 | 8/1993 | Hascoet et al. . |
| 5,300,099 | 4/1994 | Rudie . |
| 5,301,687 | 4/1994 | Wong et al. . |
| 5,323,768 | 6/1994 | Saito et al. . |
| 5,323,778 | 6/1994 | Kandarpa et al. ................ 128/653.2 |
| 5,330,518 | 7/1994 | Neilson et al. . |
| 5,344,398 | 9/1994 | Hara . |
| 5,364,392 | 11/1994 | Warner et al. ...................... 607/101 X |
| 5,370,675 | 12/1994 | Edwards et al. . |
| 5,370,676 | 12/1994 | Sozanski et al. . |
| 5,370,677 | 12/1994 | Rudie et al. ........................ 607/156 X |
| 5,370,678 | 12/1994 | Edwards et al. . |
| 5,383,917 | 1/1995 | Desai et al. . |
| 5,401,274 | 3/1995 | Kusunoki . |
| 5,405,346 | 4/1995 | Grundy et al. . |
| 5,413,588 | 5/1995 | Rudie et al. . |
| 5,437,662 | 8/1995 | Nardella . |
| 5,520,684 | 5/1996 | Imran . |
| B1 4,841,988 | 8/1990 | Fetter et al. . |

FOREIGN PATENT DOCUMENTS

| | | |
|---|---|---|
| 0 459 535 A2 | 12/1991 | European Pat. Off. . |
| 0 462 302 A1 | 12/1991 | European Pat. Off. . |
| 0 485 323 A1 | 5/1992 | European Pat. Off. . |
| 0 597 463 A2 | 5/1994 | European Pat. Off. . |
| 0 519 958 B1 | 10/1994 | European Pat. Off. . |
| 0 628 288 A2 | 12/1994 | European Pat. Off. . |
| 0 629 382 A1 | 12/1994 | European Pat. Off. . |
| 62-9351 | 2/1987 | Japan . |
| 738596 | 6/1980 | U.S.S.R. . |
| 1512622 | 10/1989 | U.S.S.R. . |
| 1 238 200 | 7/1971 | United Kingdom . |
| WO 81/03616 | 12/1981 | WIPO . |
| WO 89/11311 | 11/1989 | WIPO . |
| WO 91/13650 | 9/1991 | WIPO . |
| WO 93/20767 | 10/1993 | WIPO . |
| WO 94/02204 | 2/1994 | WIPO . |
| WO 94/22384 | 10/1994 | WIPO . |
| WO 94/26178 | 11/1994 | WIPO . |
| WO 94/26186 | 11/1994 | WIPO . |
| WO 94/26188 | 11/1994 | WIPO . |
| WO 94/28809 | 12/1994 | WIPO . |
| WO 95/05124 | 2/1995 | WIPO . |
| WO 95/05869 | 3/1995 | WIPO . |
| WO 95/17132 | 6/1995 | WIPO . |
| WO 95/17222 | 6/1995 | WIPO . |

OTHER PUBLICATIONS

Mebust et al, *Prostatic Desiccation: A Preliminary Report of Laboratory and Clinical Experience,* The Journal of Urology, vol. 108, pp. 601–603.

Mendecki, et al., *Microwave Applicators For Localized Hyperthermia Treatment of Malignant Tumors,* Journal of Bioengineering, 1977, vol. 1, pp. 511–518.

T.C. Cetas et al., *Thermometry Considerations in Localized Hyptheremia,* Medical Physics, Mar./Apr. 1978, vol. 5, No. 2, pp. 79–91.

Sugaar, et al., *A Histopathologic Study on the Effects of Radiofrequency Thermotherapy on Malignant Tumors of the Lung,* Cancer 43: 767–783, 1979.

Tabuse, *A New Operative Procedure of Hepatic Surgery Using a Microwave Tissue Coagulartor,* Arch Jap. Chir. 48(2), Mar. 1979, pp. 160–172.

Salles–Cunha, et al., *Steady Magnetic Fields in Noninvasive Electromagnetic Flowmetry,* Proceedings of the IEEE, Jan. 1980, vol. 68, No. 1, p. 149.

Magin et al., *Thermal Destruction of the Canine Prostate By High Intensity Microwaves,* Journal of Surgical Research, 29, pp. 265–275 (1980).

Mendecki et al., *Microwave Applicators for Localized Hyperthermia Treatment of Cancer of the Prostate,* Radiation Oncology Biology Physics, Nov. 1980, vol. 6, No. 11, pp. 1583–1588.

Taylor, *Implantable Radiators for Cancer Therapy By Microwave Hyperthermia,* Proceedings of the IEEE, Jan. 1980, vol. 68, No. 1, pp. 142–148.

Brezovich, et al., *A Practical System for Clinical Radiofrequency Hyperthermia,* Radiation Onocology, Biology, Physics, Mar. 1981, vol. 7, No. 3, pp. 423–430.

Sterzer, *Localized Hyperthermia Treatment of Cancer,* RCA Review, Dec. 1981, vol. 42, pp. 728–751.

Bahl, et al., *Microstrip Loop Radiators for Medical Applications,* IEEE Transactions on Microwave Theory and Techniques, Jul. 1982, vol. MTT–30, No. 7, pp. 1090–1095.

Scheiblich, et al., *Radiofrequency–Induced Hyperthermia in the Prostate,* Journal of Microwave Power, 1982, 17(3), pp. 203–209.

Li, et al., *Design and Thermometry of an Intracavitary Microwave Applicator Suitable for Treatment of Some Vaginal and Rectal Cancers,* Radiation Oncology, Biology, Physics, Nov. 1984, vol. 10, No. 11, pp. 2155–2162.

Harada, et al., *Hyperthermic Treatment with Intravesical Microwave Radiation for Bladder Cancer,* Nishi Nihon Urology, Jul. 1984, vol. 47, No. 4, pp. 1047–1051.

Ghods, et al., *An Insulated Coaxial Probe for EM Local Heating,* IEEE Transactions on Biomedical Engineering, Jun. 1985, vol. BME–32, No. 6, pp. 418–427.

Trembly, *The Effects of Driving Frequency and Antenna Length on Power Deposition Within a Microwave Antenna Array Used for Hyperthermia*, IEEE Transactions on Biomedical Engineering, Feb. 1985, vol. BME–32, No. 2, pp. 152–158.

Sathiaseelan, et al., *Clinical Microwave Hyperthermia System with Multipoint Real–Time Thermal Dosimetry*, The British Journal of Radiology, Dec. 1985, 58, pp. 1187–1195.

Harada, et al., *Microwave Surgical Treatment of Diseases of Prostate*, Urology, Dec. 1985, vol. XXVI, No. 6, pp. 572–576.

Turner, *Interstitial Equal–Phased Arrays for EM Hyperthermia*, IEEE Transactions on Microwave Theory and Techniques, May 1986, vol. MTT–34, No. 5, pp. 572–578.

Wu, et al., *Performance Characteristics of a Helical Microwave Interstitial Antenna for Local Hyperthermia*, Medical Physics, Mar./Apr. 1987, vol. 14, No. 2, pp. 235–237.

Leybovich et al., *Intracavitary Hyperthermia: A Newly Designed Applicator for Tracheal Tumors*, Endocurie Hyperthermia Oncology, Jan. 1987, vol. 3, pp. 23–29.

Torusatoh et al., *Implantable Helical Coil Microwave Antenna For Interstitial Hyperthermia*, Int. J. Hyperthermia, 1988, vol. 4, No. 5, pp. 497–512.

Astrahan, et al., *A Technique for Combining Microwave Hyperthermia with Intraluminal Brachytherapy of the Oesophagus*, Int. J. Hyperthermia, 1989, vol. 5, No. 1, pp. 37–51.

James, et al., *The Effect of Insertion Depth on the Theoretical SAR Patterns of 915 MHz Dipole Antenna Arrays for Hyperthermia*, Int. J. Hyperthermia, 1989, vol. 5, No. 6, pp. 733–747.

Astrahan, et al., *Microwave Applicator for Transurethral Hyperthermia of Benign Prostatic Hyperplasia*, Int. J. Hyperthermia, 1989, vol. 5, No. 3, pp. 283–296.

Sapozink, et al., *Transurethral Hyperthermia for Benign Prostatic Hyperplasia: Preliminary Clinical Results*, The Journal of Urology, May, vol. 143, pp. 944–950.

Debicki, et al., *Superficial and Intraurethral Applicators for Microwave Hyperthermia*, Consensus on Hyperthermia for the 1990s, 1990, pp. 321–326.

Tucker et al., *The In Vivo Effect of Regional Hyperthermia on Dunning R3327 Prostatic Tumor*, The Prostate 18:321–329 (1991).

Carter, et al., *Single–Session Transurethral Microwave Thermotherapy for the Treatment of Benign Prostatic Obstruction*, Journal of Endourology, 1991, vol. 5. No. 2, pp. 137–144.

Hurter, et al., *A Dipole Antenna for Interstitial Microwave Hyperthermia*, IEEE Transactions on Microwave Theory and Techniques, Jun. 1991, vol. 39, No. 6, pp. 1048–1053.

Buchsbaum, *RF and Microwave Fundamentals*, Buchsbaum's Complete Handbook of Practical Electronic Reference Data, pp. 272–273.

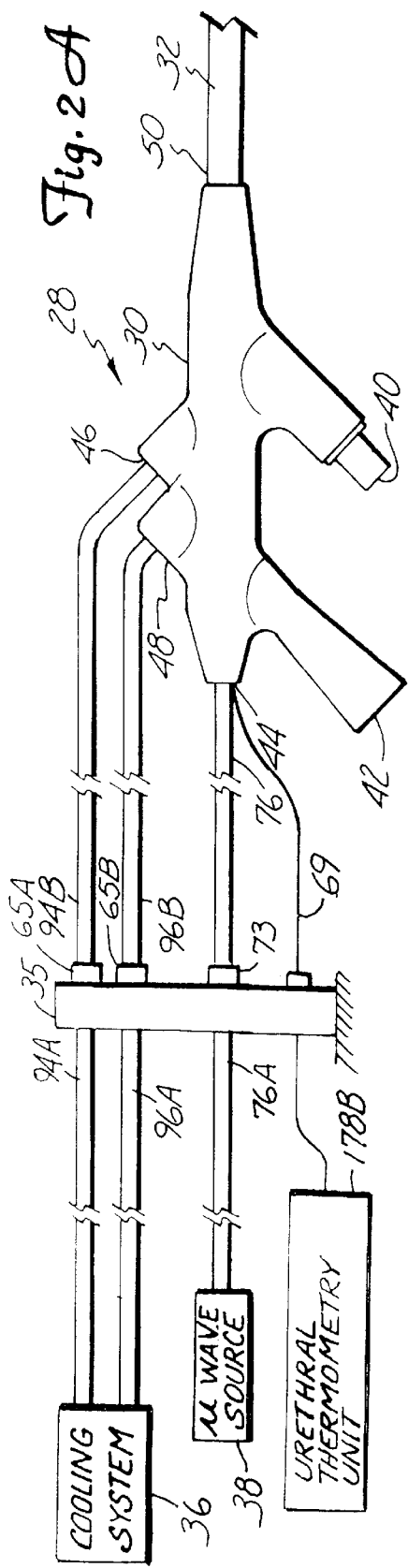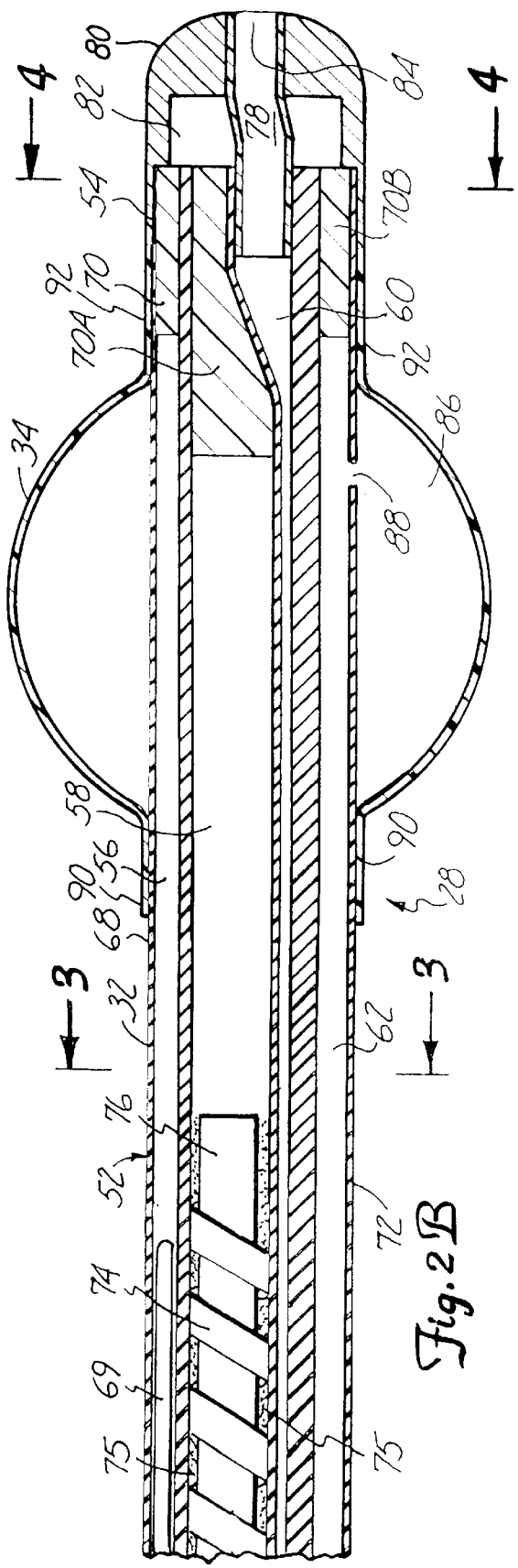

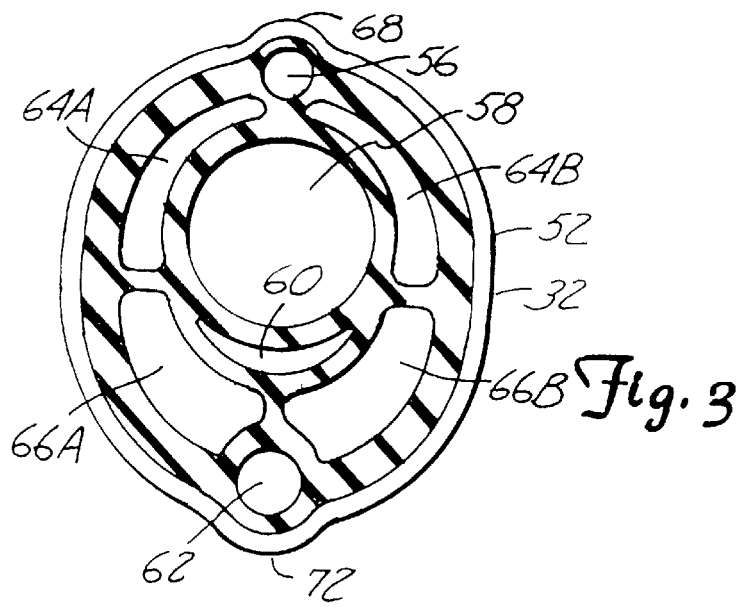
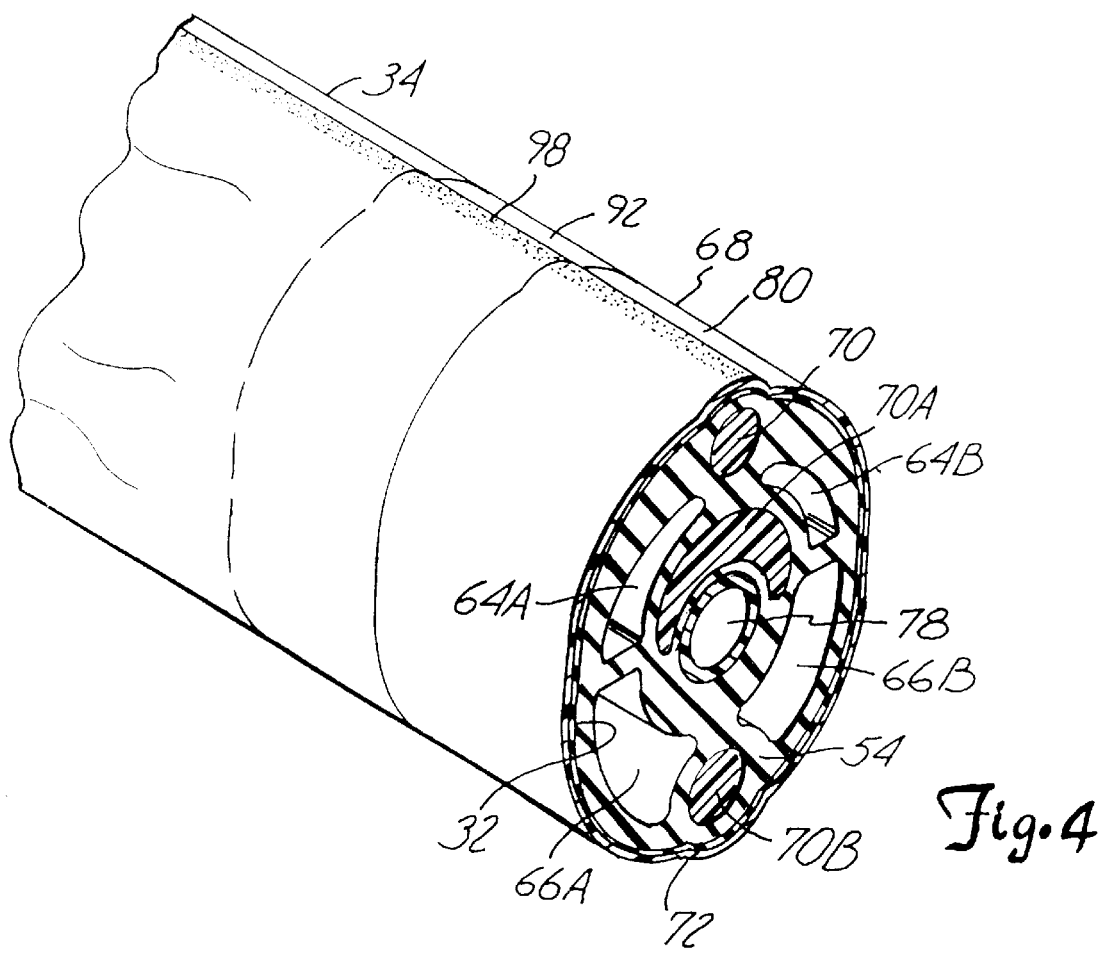

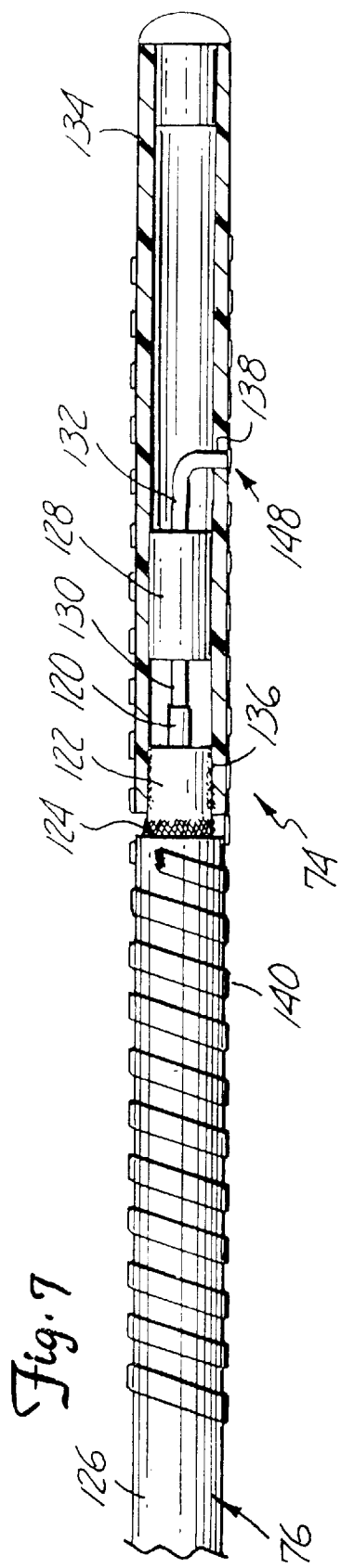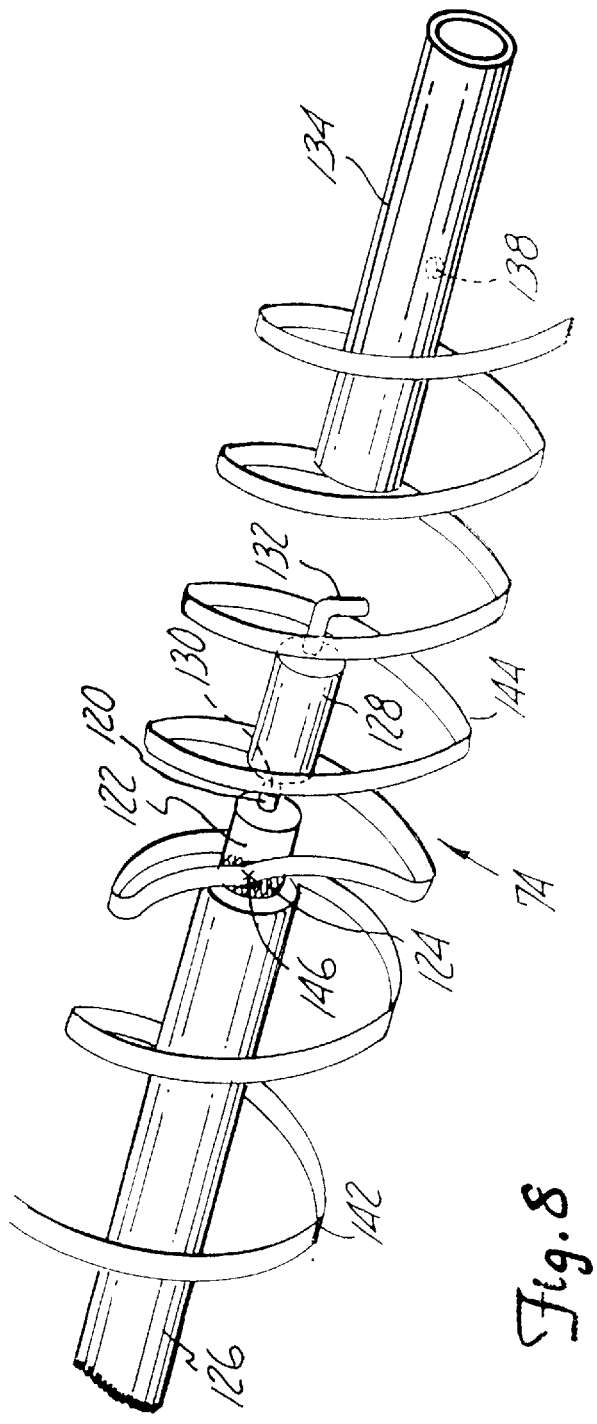

VOLTAGE CONTROLLED VARIABLE TUNING ANTENNA

REFERENCE TO CO-PENDING APPLICATIONS

This is a division of patent application Ser. No. 08/621,634, filed on Mar. 26, 1996, now U.S. Pat. No. 5,938,692, which is related to application Ser. No. 08/413,392, filed on Mar. 30, 1995, now U.S. Pat. No. 5,545,137, entitled DEVICE FOR ASYMMETRICAL THERMAL THERAPY WITH HELICAL DIPOLE MICROWAVE ANTENNA by Rudie et al., which is a divisional of patent application Ser. No. 08/208,642, filed on Mar. 9, 1994, now U.S. Pat. No. 5,464,445, entitled DEVICE AND METHOD FOR ASYMMETRICAL THERMAL THERAPY WITH HELICAL DIPOLE MICROWAVE ANTENNA by Rudie et al., which is a continuation of patent application Ser. No. 07/847,718, filed on Mar. 6, 1992, now U.S. Pat. No. 5,413,588, by Eric N. Rudie, Bruce H. Neilson and James V. Kauphusman for DEVICE AND METHOD FOR ASYMMETRICAL THERMAL THERAPY WITH HELICAL DIPOLE MICROWAVE ANTENNA.

BACKGROUND OF THE INVENTION

The present invention relates to the field of microwave thermal therapy of tissue. In particular, the present invention relates to a catheter for transurethral microwave thermal therapy of benign prostatic hyperplasia (BPH).

The prostate gland is a complex, chestnut-shaped organ which encircles the urethra immediately below the bladder. This relatively small organ, which is the most frequently diseased of all internal organs, is the site of a common affliction among older men, benign prostatic hyperplasia (BPH), as well as a more serious affliction, cancer. BPH is a nonmalignant, bilateral nodular tumorous expansion of prostate tissue occurring mainly in the transition zone of the prostate. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

A fairly recent treatment method for BPH involves microwave thermal therapy, in which microwave energy is employed to elevate the temperature of tissue surrounding the prostatic urethra above about 45° C., thereby thermally damaging the tumorous BPH tissue. Delivery of microwave energy to tumorous prostatic tissue is generally accomplished by a microwave antenna-containing applicator, which is positioned within a body cavity adjacent the prostate gland. The microwave antenna, when energized, heats adjacent tissue due to molecular excitation and generates a cylindrically symmetrical radiation pattern which encompasses and necroses the tumorous prostatic tissue. The necrosed intraprostatic tissue is subsequently reabsorbed by the body, thereby relieving an individual from the symptoms of BPH.

A safer and more effective treatment of BPH is transurethral microwave thermal therapy. This method of treatment minimizes the distance between a microwave antenna-containing applicator and the transition zone of the prostate by positioning a Foley-type catheter-bearing applicator adjacent to the prostate gland within the urethra. Due to the close proximity of the microwave antenna to the prostate, a lesser volume of tissue is exposed to the cylindrically symmetrical radiation pattern generated by the microwave antenna, thereby minimizing the amount of healthy tissue necrosed. Intraurethral applicators of the type described can be found in Turner et al. U.S. Pat. No. 4,967,765 and Hascoet et al. European Patent Application 89403199.6.

Recent improvements in transurethral thermal therapy catheter design have resulted in even more effective application of microwave radiation applied to prostatic tissue. For instance, recent transurethral catheters such as that described in Rudie U.S. Pat. No. 5,413,588, issued May 9, 1995, include shafts having a multiplicity of lumens arranged about a lumen carrying a microwave antenna. The antenna lumen is oriented nearer a first side of the catheter shaft than a second side of the catheter shaft to position the microwave radiation closer to the first side of the catheter. Cooling lumens are arranged about the microwave antenna lumen to absorb a portion of the microwave radiation so that a greater amount of microwave radiation is absorbed on a second side of the catheter shaft than the first side. This arrangement creates an asymmetrical microwave radiation pattern to permit focusing a greater amount of microwave radiation toward a selected tissue, such as prostatic tissue anterior and lateral to the urethra. This transurethral catheter design also includes a lumen to facilitate urinary drainage from the bladder through the urethra during a treatment session.

Antennas which have been used for hyperthermia have a variety of inadequacies which preclude their application to microwave thermal therapy. First, such antennas often generate heat in two forms: microwave energy and heat energy due to resistive losses of the antenna. The efficiency of these antennas has not been of much concern due to the relatively low amount of energy used to generate interstitial temperatures of between about 43° C. to 45° C. and the lack of any adverse effect these temperatures had on healthy tissue. Furthermore, it is known in the art that the shape and size of a radiation pattern generated by some microwave antennas are in part a function of how deeply the antenna is inserted into the tissue. Prior microwave dipole antennas used for hyperthermia have been unable to provide a predictable heating pattern within tissue due to the variable effects caused by the depths of insertion of the antenna into the tissue. Finally, the radiation length of these antennas has not been easily variable to accommodate the varying sizes of prostates requiring treatment. The antenna designs of the prior art relating to hyperthermia, therefore, have proven unsatisfactory for microwave thermal therapy and its attendant higher temperatures.

The objective of microwave thermal therapy is to reduce the length of a treatment session and to selectively heat and necrose only undesirous tissue, while sparing, to the greatest extent possible, adjacent healthy tissue. In order to avoid damage to tissues immediately adjacent the microwave antenna containing applicator (i.e., the urethra, the ejaculatory duct and the rectum), it is essential that the resistive losses of the antenna he reduced or optimally eliminated. The ability to eliminate resistive losses and utilize only microwave energy to heat a targeted tissue area will permit a cooling system, such as that described in co-owned application Ser. No. 07/847,718, now U.S. Pat. No. 5,413,588, to maintain safe temperatures adjacent to the applicator by absorbing and carrying away any excess heat conducted to the urethral tissues. In addition, the ability to construct an antenna capable of producing a predictable, yet selectively variable size heating pattern would aid in achieving an effective treatment of undesirous tissue while minimizing harm to healthy tissue.

SUMMARY OF THE INVENTION

The present invention is an improved helical dipole antenna for thermal treatment of interstitial tissues. The helical antenna is carried by a coaxial cable which has an outer insulator, an outer conductor, an inner insulator and an inner conductor. The coaxial cable and antenna are in turn carried by a catheter. A mid-point of the helical antenna is connected to the outer conductor of the coaxial cable so as to form first and second helical sections of approximately equal length. A voltage controlled series capacitance is connected between the coaxial cable and the helical antenna. The voltage controlled capacitance is connected between the inner conductor of the coaxial cable and a point on the second helical section. A control voltage causes the voltage controlled capacitance to match a resistive component of impedance of the antenna with a characteristic impedance of the coaxial cable. This match minimizes reflective losses of the antenna, thereby maximizing power transferred to the antenna. In one embodiment, the reflective losses of the antenna are monitored and the control voltage adjusted to maintain the reflective losses at a minimum level.

BRIEF DESCRIPTION OF THE DRAWINGS

FIG. 2A is a side view of the distal end of the urethral catheter of the present invention.

FIG. 2B is an enlarged sectional view of the proximal end of the urethral catheter of the present invention.

FIG. 3 is a cross-sectional view of the urethral catheter of FIG. 2B taken along line 3—3.

FIG. 4 is a perspective view of a proximal region of the urethral catheter with the end portion taken in section from line 4—4 of FIG. 2B.

FIG. 7 is a partial sectional view of the microwave antenna of the urethral catheter of the present invention.

FIG. 8 is an exploded view of the microwave antenna shown in FIG. 7.

DETAILED DESCRIPTION OF THE PREFERRED EMBODIMENTS

Figure 1:
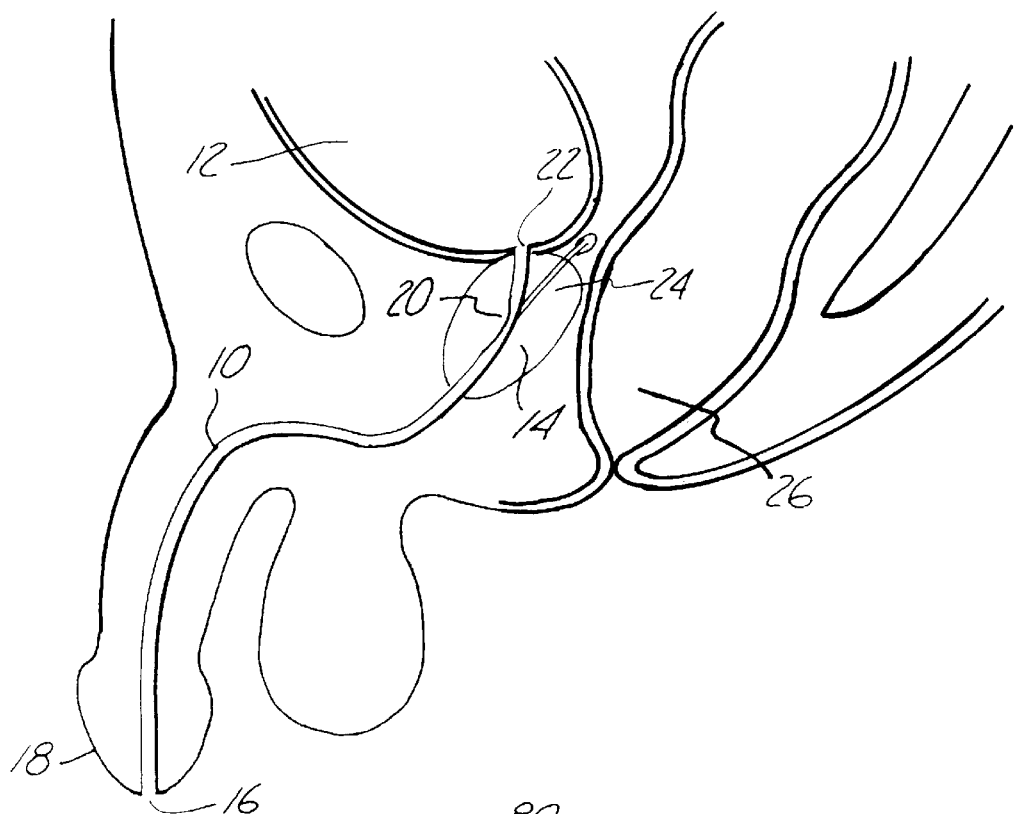
FIG. 1 is a vertical sectional view of a male pelvic region showing the urinary organs affected by benign prostatic hyperplasia.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, only periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. A selective heating of benign tumorous tissue of prostate 14 (transurethral thermal therapy) is made possible by microwave antenna-containing catheter 28 of the present invention, which is shown in FIGS. 2A and 2B.

FIG. 2A shows a side view of a distal end of catheter 28. FIG. 2B shows an enlarged sectional view of a proximal end of catheter 28. As shown in FIGS. 2A and 2B, catheter 28 generally includes multi-port manifold 30, multi-lumen shaft 32, shaft position retention balloon 34, connection manifold 35, cooling system 36 and microwave generating source 38.

Manifold 30 includes inflation port 40, urine drainage port 42, microwave antenna port 44, cooling fluid in port 46 and cooling fluid out port 48. Ports 40–48 communicate with corresponding lumens within shaft 32. Manifold 30 is preferably made of medical-grade silicone sold by Dow Corning under the trademark Silastic Q-7-4850.

Shaft 32 is connected to manifold 30 at shaft distal end 50. Shaft 32 is a multi-lumen, Foley-type urethral catheter shaft which is extruded from a flexible, medical-grade silicone sold by Dow Corning under the trademark Silastic Q-7-4850. Shaft 32, which has an outer diameter of about 16 French, includes outer surface 52, which is generally elliptical in cross-section as shown in FIG. 3. Shaft 32 is long enough to permit insertion of proximal shaft end 54 through urethra 10 and into bladder 12. In one preferred embodiment, shaft 32 is coated with a hydrophilic solution sold by Hydromer, Inc. under the mark Hydromer, which lubricates outer surface 52 of shaft 32 and facilitates its advancement within urethra 10.

As shown in FIGS. 2B–4, shaft 32 includes temperature sensing lumen 56, microwave antenna lumen 58, urine drainage lumen 60, balloon inflation lumen 62, cooling fluid intake lumens 64A and 64B, and cooling fluid exhaust lumens 66A and 66B. Lumens 56–66B generally extend from distal shaft end 50 to proximal shaft end 54.

Alternative embodiments of multi-lumen shaft 32 are also contemplated and may include different or modified cross-sections from that shown in FIGS. 2B–4. An example of an alternative embodiment of multi-lumen shaft 32 is shown and described in co-pending U.S. patent application Ser. No. 08/469,201, filed Jun. 6, 1995, now U.S. Pat. No. 5,628,770 and is hereby incorporated by reference.

As seen in FIGS. 2B–4, temperature sensing lumen 56 is positioned near first side 68 of shaft 32. Temperature sensing lumen 56 communicates with microwave antenna port 44 and permits insertion of thermometry sensor 69 within shaft 32 to monitor the temperature of surrounding tissue when shaft 32 is inserted within urethra 10. Sensor 69 exits through port 44 and is connected through connection manifold 35 to urethral thermometry unit 178B (shown in FIG. 9). In a preferred embodiment, thermometry sensor 69 is a fiber optic luminescence type temperature sensor sold by Luxtron Corporation. Temperature sensing lumen 56 is sealed at proximal end 54 by silicone plug 70.

Microwave antenna lumen 58 is eccentric to the longitudinal axis of shaft 32, antenna lumen 58 being positioned nearer first side 68 of shaft 32 than second side 72 of shaft 32. Antenna lumen 58 is sealed at proximal end 54 by silicone plug 70A. At its distal end, antenna lumen 58 communicates with microwave antenna port 44. Microwave antenna 74 is permanently positioned within antenna lumen 58 near balloon 34. Antenna 74 is positioned within antenna lumen 58 so as to be generally situated adjacent the benign tumorous tissue of prostate 14 when shaft 32 is properly positioned within urethra 10. As shown in FIGS. 2A–2B, antenna 74 is bonded within antenna lumen 58 by adhesive bond 75. Antenna 74 is carried at the proximal-most end of coaxial cable 76. The distal-most end of coaxial cable 76 is connected to connection manifold 35 by a conventional quick-coupling fitting 73. Coaxial cable 76 communicates with microwave generating source 38 by connection cable 76A, which is connected between microwave generating source 38 and connection manifold 35. In one embodiment, connection cable 76A is a standard RG 400 coaxial cable. Microwave generating source 38 produces a maximum of 100 watts of electrical power at about 915 MHz frequency, +/−13 MHz, which is within the FCC-ISM standards. When antenna 74 is energized by microwave generating source 38, antenna 74 emits electromagnetic energy which causes heating of tissue within prostate 14.

Urine drainage lumen 60 is positioned adjacent antenna lumen 58, between antenna lumen 58 and second side 72. Urine drainage lumen 60 communicates with urine drainage port 42 and defines a drainage path for urine when proximal end 54 of shaft 32 is inserted within bladder 12. Urine drainage lumen 60 is connected to urine drainage lumen extension 78 at proximal end 54. Urine drainage lumen extension 78 is bonded within proximal end cap 80. End cap 80 is further bonded over outer surface 52 of shaft 32 at proximal shaft end 54, with cavity 82 surrounding lumen extension 78. With end cap 80 and urine drainage lumen extension 78 in place, opening 84 to lumen extension 78 permits urine to drain from bladder 12 through urine drainage lumen 60 and out urine drainage port 42 when proximal shaft end 54 is inserted within bladder 12. Drainage of urine from bladder 12 is necessary due to frequent bladder spasms which occur during transurethral thermal therapy.

Balloon inflation lumen 62 is positioned near second side 72, generally between urine drainage lumen 60 and second side 72. Balloon inflation lumen 62 communicates with inflation port 40 and is sealed at proximal end 54 by silicone plug 70B. Balloon inflation lumen 62 communicates with interior 86 of balloon 34 by opening 88.

Figure 5:
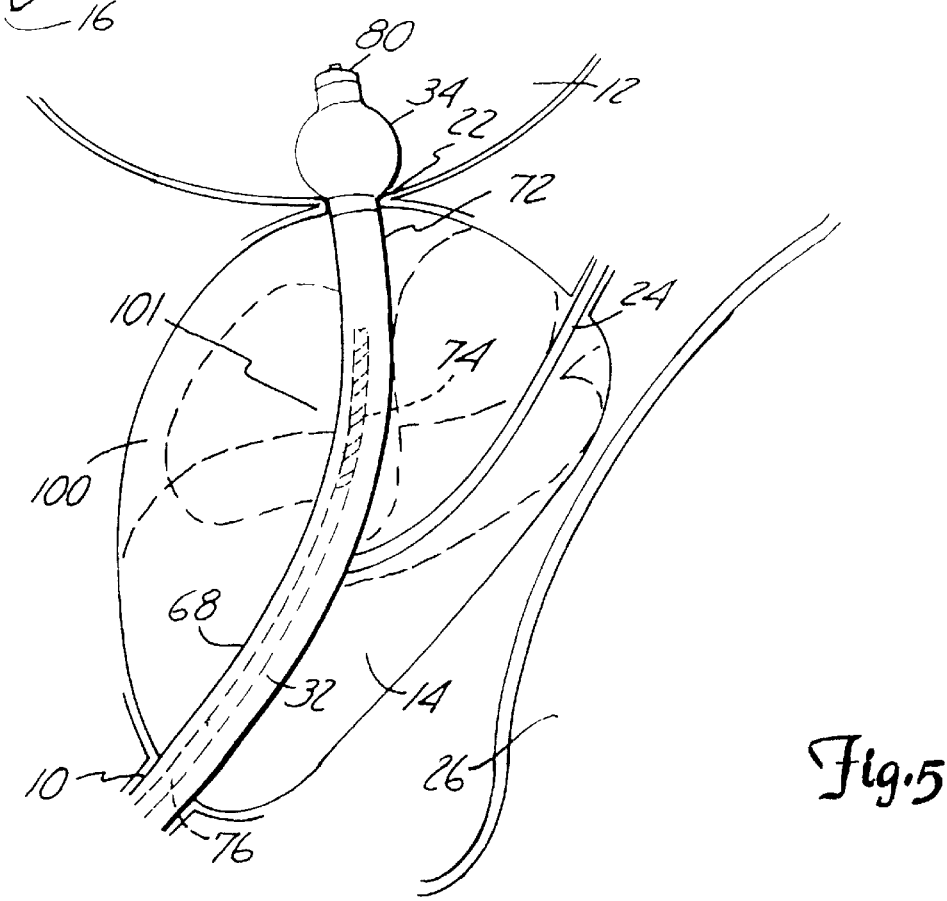
FIG. 5 is an enlarged view of the male pelvic region of FIG. 1 showing the urethral catheter of the present invention positioned within the prostate region.

Balloon 34, which is formed from a tubular section of a flexible, medical-grade silicone sold by Dow Corning under the trademark Silastic Q-7-4720, is secured over shaft 32 by bonding balloon waists 90 and 92 over exterior surface 52 of shaft 32 near proximal shaft end 54. Balloon 34 is inflated by an inflation device 188 (shown in FIG. 9), which is connected to inflation port 40 and which supplies positive fluid pressure to interior 86 of balloon 34. Balloon 34 is deflated when inflation device 188 supplies a negative fluid pressure (i.e., a vacuum) to interior 86 of balloon 34. Balloon 34 serves to retain shaft 32 in a fixed position within urethra 10 when balloon 34 is inflated within bladder 12 near bladder neck 22, as shown in FIG. 5.

As shown in FIGS. 2B–4, cooling fluid intake lumens 64A, 64B are positioned circumjacent first side 68, between first side 68 and antenna lumen 58. Cooling fluid intake lumens 64A, 64B extend from distal shaft end 50 to proximal shaft end 54 where lumens 64A, 64B are exposed to cavity 82 of end cap 80. Intake lumens 64A, 64B are relatively narrow in cross-section and have a relatively small cross-sectional surface area. Water contained within intake lumens 64A, 64B performs two essential functions. First, water contained within lumens 64A, 64B absorbs some of the microwave energy emitted by antenna 74. This assists, in part, in controlling the volume of tissue adjacent first side 68 of shaft 32 that is heated above about 45° C. Second, the water within lumens 64A, 64B absorbs heat energy generated by the microwave energy from adjacent tissues (i.e., urethra 10) via thermal conduction. This prevents the portion of urethra 10 adjacent first side 68 from being overheated and damaged when antenna 74 is energized.

Cooling fluid exhaust lumens 66A, 66B are circumjacent second side 72 with lumens 66A, 66B generally positioned between second side 72 and antenna lumen 58. Like intake lumens 64A, 64B, exhaust lumens 66A, 66B extend from shaft distal end 50 to shaft proximal end 54 where exhaust lumens 66A, 66B are exposed to cavity 82 of end cap 80. Exhaust lumens 66A, 66B are wider in cross-section than intake lumens 64A, 64B, and have a cross-sectional area greater than the cross-sectional area of intake lumens 64A, 64B. Water within exhaust lumens 66A, 66B is therefore capable of absorbing a greater amount of microwave energy when antenna 74 is energized. As a result, for a given power output from microwave generating source 38, the temperature of tissue adjacent second side 72 will remain below about 45° C. Water within exhaust lumens 66A, 66B also absorbs heat energy from adjacent tissue (i.e., urethra 10) when antenna 74 is energized, which prevents the portion of urethra 10 adjacent second side 72 from being overheated and damaged when antenna 74 is energized.

Intake lumens 64A, 64B and exhaust lumens 66A, 66B are supplied with deionized water from cooling system 36. Water from cooling system 36 is chilled to between about 12–15° C. and pumped at a rate of between about 100–150 milliliters per minute via water feed line 94A to connection manifold 35. Alternatively, water from cooling system 36 may be chilled to between about 1–15° C. and pumped at a rate of between about 25–250 milliliters per minutes via water feed line 94A to connection manifold 35, as described in co-pending U.S. patent application Ser. No. 08/309,137, filed Sep. 20, 1994, now U.S. Pat. No. 5,620,480, which is hereby incorporated by reference. The water flows through connection manifold 35 to water feed line 94B and to water intake port 46, which communicates with water intake lumens 64A, 64B. Under fluid pressure, the water circulates through intake lumens 64A, 64B to cavity 82 of end cap 80. The water returns to cooling system 36 through exhaust lumens 66A, 66B to fluid exhaust port 48. The water is carried from water exhaust port 48 via water return line 96B to connection manifold 35, and from connection manifold 35 to cooling system 36 via water return line 96A. The water is then re-chilled and re-circulated. Water feed line 94B and water return line 96B are each provided with a conventional quick-coupling fitting 65A and 65B, respectively, which permits catheter 28 to be easily disconnected from cooling system 36.

FIG. 5 shows an enlarged view of the male pelvic region of FIG. 1 with catheter 28 properly positioned within urethra 10. Orientation stripe 98 along exterior surface 52 on first side 68, as shown in FIG. 4, ensures the proper orientation of shaft 32 within urethra 10. As shown in FIG. 5, shaft 32 is positioned within urethra 10 with second side 72 of shaft 32 oriented toward rectum 26. Water exhaust lumens 66A, 66B are oriented posteriorly, toward rectum 26 and water intake lumens 64A, 64B are oriented anteriorly toward fibromuscular tissue 100 of prostate 14. The portion of transition zone 101 anterior and lateral to urethra 10 is the most frequent location of the tumorous tissue growth which causes BPH. Since water exhaust lumens 66A, 66B are capable of absorbing more microwave energy than water intake lumens 64A, 64B, the radiation patterns created by microwave energy emitted from antenna 74 are asymmetrical. Thus, a relatively large volume of tissue enveloping the anterior portion of transition zone 101, adjacent first side 68.

is heated to a temperature above about 45° C., which effectively necroses the tumorous tissue of prostate 14 which encroaches upon urethra 10. In comparison, the temperature of tissue adjacent second side 72 remains below about 45° C., thereby eliminating the harmful effects of the microwave energy to ejaculatory duct 24 and rectum 26.

Figure 6:
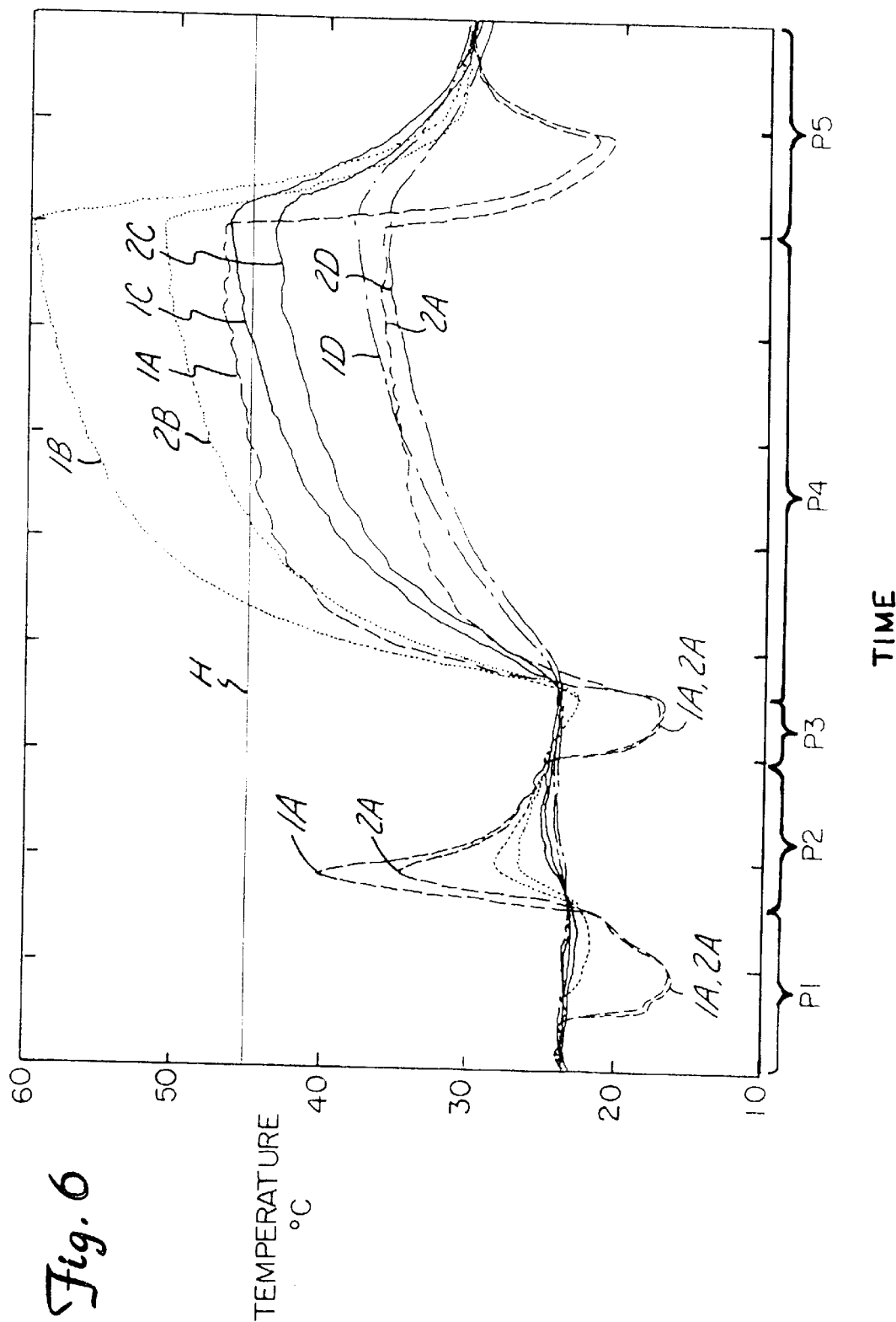
FIG. 6 is a graph illustrating temperature distribution generated by the catheter of the present invention as a function of time.

FIG. 6 is a graph which generally demonstrates a microwave thermal therapy procedure and a temperature distribution which was generated by catheter 28 of the present invention, with shaft 32 inserted into a polyacrylamide gel formulation which simulates biological tissue. The formulation and preparation procedures for the polyacrylamide gel are discussed in detail in D. Andreuccetti, M. Bini, A. Ignesti, R. Olmi, N. Rubino, and R. Vanni, *Use of Polyacrylamide as a Tissue-Equivalent Material in the Microwave Range*, 35 IEEE TRANSACTIONS ON BIOMEDICAL ENGINEERING 275 (No. 4, April 1988). FIG. 6 shows temperature measurements taken from eight temperature sensors. Four sensors were aligned at fixed distances adjacent first side 68. Sensor 1A was positioned immediately adjacent shaft 32; sensor 1B was positioned about 0.66 cm from shaft 32: sensor 1C was positioned about 1.33 cm from shaft 32; and sensor 1D was positioned about 2.0 cm from shaft 32.

Four sensors were also aligned at fixed distances adjacent second side 72. Sensor 2A was positioned immediately adjacent shaft 32; sensor 2B was positioned about 0.66 cm from shaft 32; sensor 2C was positioned about 1.33 cm from shaft 32; and sensor 2D was positioned about 2.0 cm from shaft 32.

The x-axis represents a relative period of time over which the microwave thermal therapy procedure was performed. The y-axis represents temperature in degrees Celsius, with horizontal line H representing 45° C. (the temperature at or above which cells are necrosed).

As generally shown in FIG. 6, the microwave thermal therapy procedure of the present invention includes five operating phases, P1–P5. Lines 1A–1D and 2A–2D correspond with sensors 1A–1D and 2A–2D, respectfully. During first phase P1, cooling system 36 is turned on and chilled water is pumped through cooling lumens 64A, 64B and 66A, 66B. A drop in temperature immediately adjacent shaft 32 is represented by lines 1A, 2A. At the end of first phase P1, cooling system 36 is turned off. At the beginning of second phase P2, a relatively small amount of power (about 5 watts) is applied to microwave antenna 74. The temperature immediately adjacent shaft 32 rises asymmetrically due to the greater absorptivity of water in the larger exhaust lumens 66A, 66B on second side 72, as shown by lines 1A, 2A. The power is applied long enough to merely warm adjacent tissue to about 40° C. By the end of second phase P2, temperatures generally return to base line temperature.

In a preferred embodiment of the present invention, the tissue responses to the chilling during P1 and the heating during P2 aid in determining the vascularity of the tissue to be treated. This information aids in determining the amount of power necessary to treat tumorous tissue of prostate 14.

At the beginning of third phase P3, cooling system 36 is again turned on thereby pumping chilled water through cooling lumens 64A–66B. The temperature immediately adjacent shaft 32 correspondingly drops as indicated by lines 1A, 2A. Prechilling of the tissue immediately adjacent shaft 32 aids in protecting the tissues immediately adjacent shaft 32 (i.e., urethra 10) from overheating due to a relatively rapid application of power from antenna 74.

Microwave generating source 38 is again turned on at the beginning of fourth phase P4 at a sustained power output of about 20 watts. As shown in FIG. 6, due to the absorptivity differential between water in the narrower intake lumens 64A, 64B and water in the wider exhaust lumens 66A, 66B, temperatures adjacent second side 72, represented by lines 2A–2D, are cooler than temperatures adjacent first side 68, represented by lines 1A–1D. The temperature differentials are most profound within a target volume of tissue 0.66 cm from shaft 32. Within this target volume, as shown by lines 1A, 2A and 1B, 2B, the difference in temperature from first side 68 and second side 72 is on the order of about 10° C. Thus, by adjusting cooling system parameters or power output from microwave generating source 38, tissue within 0.66 cm of first side 68 can be heated to temperatures at or above about 45° C., while tissue within 0.66 cm of second side 72 can remain at temperatures substantially below 45° C. In this manner, tissue-necrosing temperatures within the target volume are essentially restricted only to tissue near first side 68, which is the most frequent location of periurethral tumorous prostatic tissue. Alternatively, by adjusting the power output or cooling system parameters, a relatively small volume of tissue adjacent second side 72 can be heated above about 45° C. to necrose some of the tumorous prostatic tissue which is posterior and lateral to the urethra. In the preferred embodiment, during fourth phase P4, microwave generating source 38 is operated for at least about 45 minutes.

As shown by lines 1A, 2A, during P4, the temperature of tissue immediately adjacent shaft 32 (which is representative of temperatures of urethra 10), as well as temperatures of tissue beyond 0.66 cm from shaft 32, as shown by lines 1C, 2C and 1D, 2D, are maintainable well below 45° C. This is accomplished by adjusting cooling system parameters and, if necessary, power output from microwave generating source 38.

At the end of fourth phase P4 power is turned off. At the beginning of fifth phase P5, cooling system 36 continues to operate, circulating water through cooling lumens 64A–66B. A temperature drop immediately adjacent shaft 32 is relatively rapid as shown by lines 1A, 2A within P5. In a preferred embodiment of the present invention, cooling system 36 continues to operate for a period of time (on the order of 10 to 120 minutes) after the procedure to cool urethra 10 and reduce edema resulting from the application of heat to the periurethral tissues of prostate 14. In an alternative embodiment, water feed line 94B, water return line 96B and thermometry sensor 69 (as shown in FIG. 2A) are disconnected from connection manifold 35. Water feed line 94B and water return line 96B of catheter 28 are then connected to another cooling system similar to cooling system 36 and water is then circulated through cooling lumens 64A–66B in a manner similar to that previously described. In this fashion, recovery from the previously described procedure can be accomplished away from the treatment area thereby enabling microwave generating source 38 and cooling system 36 to be readily available for treatment of another patient.

FIG. 7 shows a partial sectional view of microwave antenna 74 of the present invention. Antenna 74 is positioned at a proximal-most end of shielded coaxial cable 76. Cable 76 is a standard RG 178U coaxial cable and includes inner conductor 120, inner insulator 122, outer conductor 124, and outer insulator 126. Outer insulator 126, outer conductor 124 and inner insulator 122 are stripped away to expose about 3 millimeters of outer conductor 124, about 1 millimeter of inner insulator 126 and about 1 millimeter of inner conductor 120. Capacitor 128 includes first end 130, which is connected to inner conductor 120 by soldering, and second end 132, which connects to antenna 74. Capacitor 128 serves to counteract a reactive component of antenna 74, thereby providing a 50 ohm match between coaxial cable 76 and microwave generating source 38, and antenna 74.

In another embodiment of antenna 74, capacitor 128 is replaced with a tubular-shaped capacitor (not shown). The construction of the alternative embodiment of antenna 74 using a tubular-shaped capacitor is described in co-owned U.S. Pat. No. 5,370,677, issued Dec. 6, 1994, which is hereby incorporated by reference.

Tubular extension 134, which is a hollow section of outer insulator 126 of coaxial cable 76, is positioned over capacitor 128 and the exposed length of inner insulator 122 and secured by bond 136. Tubular extension 134 includes hole 138, which provides an exit for second end 132 of capacitor 128. Wound about outer insulator 126 and tubular extension 134 is flat wire 140. Flat wire 140 is a single piece of flat copper wire with dimensions of about 0.009 inch by about 0.032 inch in cross-section, which provides a relatively large surface area for maximum current flow while minimizing the cross-sectional size of antenna 74.

FIG. 8 is an exploded view of a portion of antenna 74 which shows its helical dipole construction. Generally, the efficiency of any dipole antenna is greatest when the effective electrical length of the antenna is generally one half the wavelength of the radiation emitted in the surrounding medium. Accordingly, a relatively efficient simple dipole antenna, operating at about 915 MHz, would require a physical length of about 8 centimeters which, according to the present invention, would needlessly irradiate and damage healthy tissue. Furthermore, the physical length of a relatively efficient simple dipole antenna operating at about 915 MHz cannot be varied.

As shown in FIG. 8, flat wire 140 is soldered to outer conductor 124 at solder point 146. Flat wire 140 is then wound in a distal direction about outer insulator 126 and in a proximal direction about tubular extension 134, thereby forming first wire section 142 and second wire section 144, both of which are of equal length. In one embodiment, first and second wire sections 142 and 144 are each comprised of eight, equally-spaced windings of flat wire 140. The combined length of first and second wire sections 142 and 144, and hence the overall length of antenna 74, ranges from about 1.5 centimeters to about 4.0 centimeters, and varies according to the length of the area of prostate 14 which requires treatment. A standard medical-grade silicone tube (not shown), which has been allowed to soak in a solvent, such as Freon, is positioned over first and second wire sections 142 and 144. As the solvent evaporates, the silicone tube shrinks, thereby securing flat wire 140 to outer insulator 126 and tubular extension 134.

The helical dipole construction of the present invention, allows antenna 74 to range in physical length from about 1.5 to 4 centimeters, while electrically behaving like an eight centimeter-long simple dipole antenna. In other words, antenna 74 has an effective electrical length generally equal to one half of the wavelength of the radiation emitted in the surrounding medium, independent of its physical length. For purposes of definition, the surrounding medium includes the catheter shaft and the surrounding tissue. This is accomplished by varying the number and pitch of the windings of first and second wire sections 142 and 144. A family of catheters, which contain relatively efficient helical dipole antennas of different physical lengths, permits selection of the antenna best suited for the particular treatment area. In addition, antenna 74 of the present invention is capable of producing a constant heating pattern in tissue, concentrated about antenna 74, independent of the depth of insertion into the tissue.

Second end 132 of capacitor 128, which exits hole 138, is soldered to second wire section 144 at tap point 148, as shown in FIG. 7. Tap point 148 is a point at which the resistive component of the combined impedance of first wire section 142 and second wire section 144 matches the characteristic impedance of coaxial cable 76. The impedance of either first wire section 142 or second wire section 144 is expressed as Z, where $Z=R+jX$. The impedance Z varies from a low value at solder point 146 to a high value at a point farthest from solder point 146. There exists a tap position where R is equal to 50 ohms, but an imaginary component, X, is inductive. This inductive component can be canceled by inserting a series capacitance, such as capacitor 128, which has a value of $-jX$ ohms. This results in an impedance match of 50 ohms real. The resulting method of feeding antenna 74 is commonly called gamma matching. In one embodiment of the present invention, where the physical length of flat wire 140 is about 2.8 cm, tap point 148 is about 3.5 turns from solder point 146 on second wire section 144. In the preferred embodiment, the value of capacitor 128 is about 2.7 pF.

The helical dipole construction of antenna 74 achieves a relatively small size, which permits intraurethral application. The helical dipole construction is also responsible for three features which enable antenna 74 to achieve greater efficiency than prior known interstitial microwave antennas: good impedance matching, good current carrying capability and an effective electrical length which is generally one half of the wavelength of the radiation emitted in the surrounding medium, independent of the physical length of antenna 74.

First, the good impedance match between antenna 74 and inner conductor 120 minimizes reflective losses of antenna 74, with measured reflective losses of less than 1% in a preferred embodiment. Second, the use of flat ribbon wire 140 for first wire section 142 and second wire section 144 minimizes resistive losses of antenna 74 by providing a greater surface area upon which RF current can be carried. Finally, the helical dipole design of antenna 74 has an effective electrical length which is generally one half of the wavelength of the radiation emitted in the surrounding medium, independent of the physical length of antenna 74. This permits the physical length of antenna 74 to be varied to accommodate varying sizes of individual prostates while maintaining the same efficient, effective electrical length of antenna 74.

The use of an efficient microwave antenna is critical to the ability to focus thermal energy a distance from the antenna within a target volume. An inefficient antenna produces a lesser intensity of microwave radiation within the target volume than desired. It also produces undesired heat close to the urethra, which will damage the urethra if not carried away by an increased coolant flow. This added burden on the cooling system reduces its capacity to protect the urethra, thereby limiting the microwave power that can be radiated without elevating urethra temperatures above safety limits. With microwave power limited by cooling system capacity, the heat delivered to the desired target area of the prostate will not be sufficient for effective therapy. The efficient helical dipole design of antenna 74 of the present invention, however, ensures that almost all heat delivered during the treatment is delivered in the form of microwave energy, rather than conductive heat energy.

Figure 9:
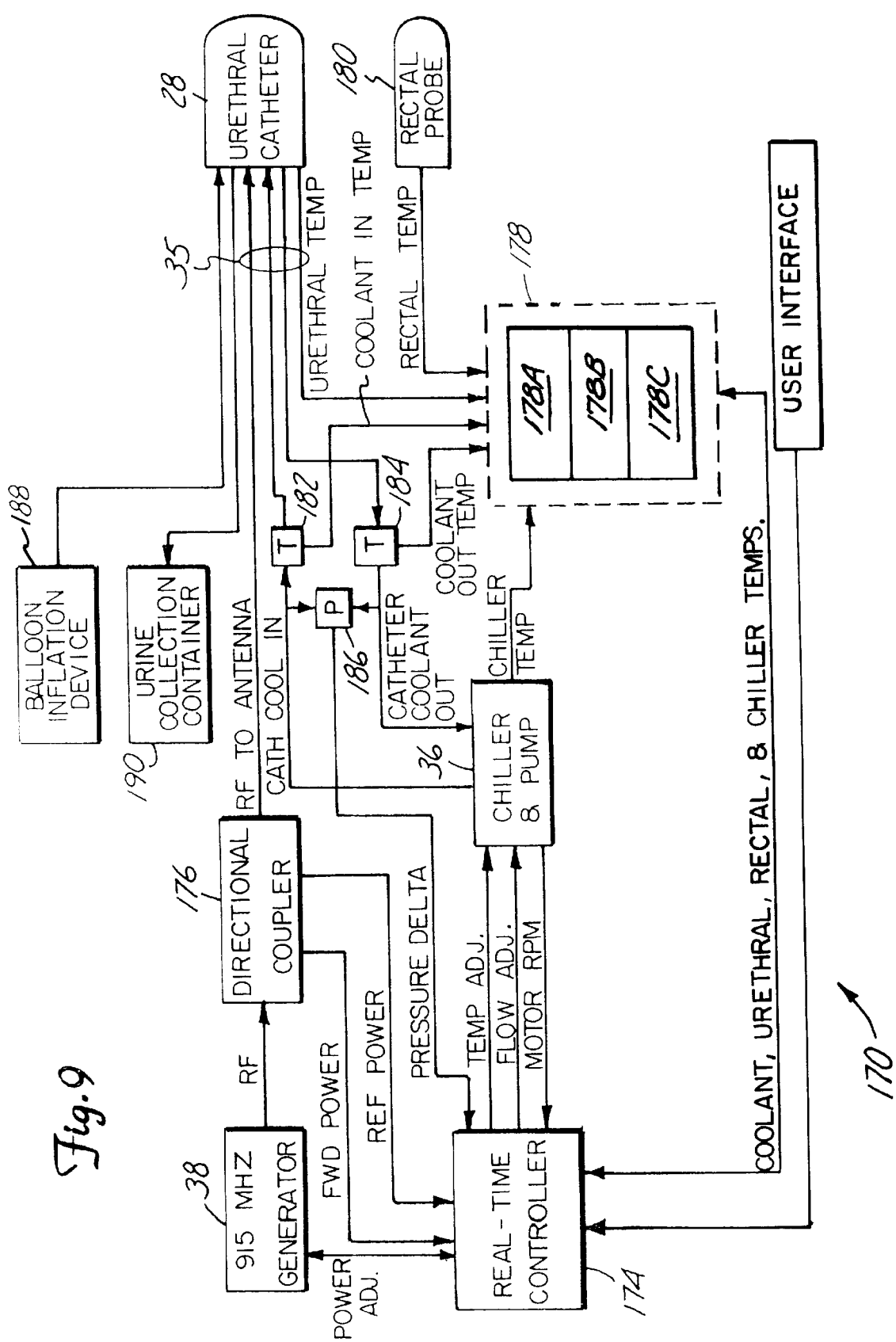
FIG. 9 is a block diagram of the transurethral microwave thermal therapy system of the present invention.

FIG. 9 is a block diagram of transurethral microwave thermal therapy system 170, with which urethral catheter 28 is used. System 170 includes cooling system 36 microwave generating source 38, user interface 172, real time controller (RTC) 174, directional coupler 176, thermometry sensors 182 and 184, coolant pressure sensor 186, balloon inflation device 188, and urine collection container 190.

As shown in FIG. 9, control of microwave generating source 38 and cooling system 36 is affected by real time controller 174, which is in turn controlled by user interface 172. User interface 172 is an IBM compatible machine including a hard drive and a solid state memory device for data storage. User interface 172 communicates with RTC 174, which is responsible for all closed loop feedback to run system 170. RTC 174 has direct closed loop control of microwave power from microwave generating source 38, and coolant flow and coolant temperature of cooling system 36. The closed loop feedback tracks out variations in gain, drift and cable losses inherent in microwave generating source 38, and variability in pump output and refrigeration system efficiency of cooling system 36. In addition to monitoring microwave generating source 38 and cooling system 36, RTC 174 also monitors and controls several channels of thermometry via inputs from thermometry unit 178. Cooling system thermometry 178A measures the coolant and chiller temperatures based upon signals from coolant temperature sensors 182 and 184 and a chiller temperature sensor (not shown) of cooling system 36. Urethral thermometry 178B measures urethral temperature based upon signals from temperature sensor 69 within catheter 28. Rectal thermometry 178C measures rectal temperature based upon signals received from a sensor (not shown) within rectal probe 180.

RTC 174 transmits all closed-loop feedback to user interface 172, which processes the input and transmits corrections and instructions back to RTC 174. RTC 174 interprets the instructions given to it by process control language received from user interface 172 and executes the instructions in real time. All corrections from user interface 172 are made to maintain a given thermal profile throughout the transurethral thermal therapy. In addition, system 170 includes a hardware fail-safe circuit which shuts down system 170 should any parameter fall outside a given range of values.

Figure 10:
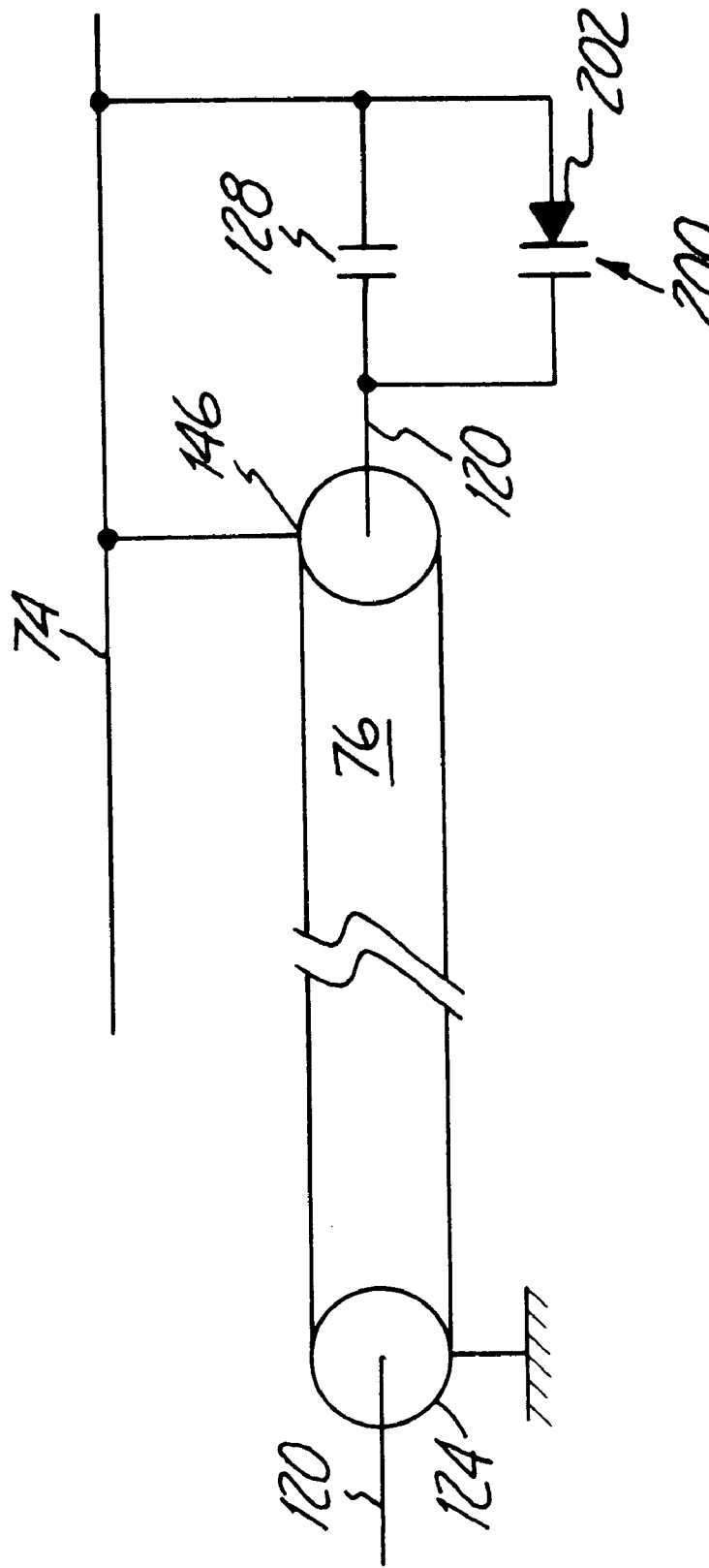
FIG. 10 is a schematic diagram of an alternative embodiment of the present invention.

FIG. 10 schematically illustrates an impedance matching means 200 used in another embodiment of antenna 74. Impedance matching means 200 provides a variable and controllable capacitance for aiding capacitor 128 in counteracting the reactive component of antenna 74. Variable impedance matching means 200 allows the impedance of microwave generating source 38, coaxial cable 76, and antenna 74 to be accurately matched throughout the thermal therapy process. As noted above, accurate impedance matching allows the antenna's reflected power to be minimized.

A variable and controllable capacitance is desired for several reasons. A variable and controllable capacitance allows greater manufacturing variability to be tolerated in antenna 74, coaxial cable 76, microwave generating source 38, and catheter 28, for example. Greater tolerances lower the manufacturing expense, but the increased tolerances in antenna 74, coaxial cable 76, microwave generating source 38, and catheter 28, for example, also introduce variations in the impedance of the system. A variable and controllable capacitance can help compensate for the variations in impedance created by greater manufacturing tolerances. Also, as the microwave thermal therapy progresses, the resistivity and permeability characteristics of the tissue change, thereby affecting the impedance match between of antenna 74 and coaxial cable 76. A variable and controllable capacitance is helpful in maintaining the impedance match between the antenna 74 and the coaxial cable 76. In sum, there are a wide variety of factors which may cause the accuracy of the impedance match between antenna 74 and coaxial cable 76 to vary, and it is desirable to be able to adjust antenna 74 to account for those variations.

Presently, the impedance match between antenna 74 and coaxial cable 76 may be adjusted by altering the frequency of the energy supplied to antenna 74. However, the range of adjustment for accurately matching the impedance of antenna 74 and coaxial cable 76 in this manner is limited by the acceptable range of frequencies for microwave thermal therapy. The adjustment range made available by altering the frequency may not always be sufficient to accurately match the impedance of antenna 74 and coaxial cable 76, particularly if the use of a single frequency or narrow frequency range is desired. It is therefore desirable to extend the range of adjustment by other means.

The use of variable impedance matching means 200 improves the ability to "tune" antenna 74 and match the impedance of antenna 74 to coaxial cable 76. Variable impedance matching means 200 may be used together with frequency alteration to extend the range of adjustment provided by altering the frequency of the microwave energy supplied to antenna 74. Alternatively, variable impedance matching means 200 may be used alone to match the impedance of antenna 74 and coaxial cable 76, especially where it is desired to use a single frequency during the therapy.

Impedance matching means 200 is preferably a reverse biased diode 202 connected in parallel with capacitor 128 between antenna 74 and inner conductor 120 of coaxial cable 76. Reverse biased diode 202 can be a varactor diode, a pin diode, or other diode capable of acting in reverse biased fashion. Suitable diodes, for example, are square ceramic MELFs available from Alpha Industries, Inc., of Woburn, Mass. under part numbers A60030P535, A60033P535 and A60036P535. Reverse biased diode 202 provides a voltage dependant capacitance which may be altered by changing the external voltage which is applied to the diode 202. Preferably, reverse biased diode 202 has a capacitance range sufficient to accommodate catheter and patient variability.

As shown in FIG. 10, impedance matching means 200 is preferably located at, or as close as possible to antenna 74 to aid in obtaining an accurate impedance match between antenna 74 and coaxial cable 76. By locating impedance matching means 200 at, or close to antenna 74, a more accurate impedance match may be obtained. However, it is possible to locate impedance matching means 200 remotely from antenna 74 if a less accurate impedance match is acceptable. For example, impedance matching means 200 may be located near manifold 30, rather than near antenna 74. It may be desired to locate variable impedance matching means 200 remotely from antenna 74 if the size of variable impedance matching means 200 prohibits its location within catheter 28.

While FIG. 10 depicts variable impedance matching means 200 as used in parallel with capacitor 128, it is also contemplated that the variable impedance matching means 200 be used as the only impedance matching means (i.e., without capacitor 128). If a variable impedance matching means 200 has a capacitance of sufficient size, there is no need for additional capacitor 128. The use of capacitor 128 and variable impedance matching means 200 in parallel may be required if, for example, variable impedance matching means 200 does not have a capacitance large enough to match the impedance of antenna 74 to coaxial cable 76.

Figure 11:
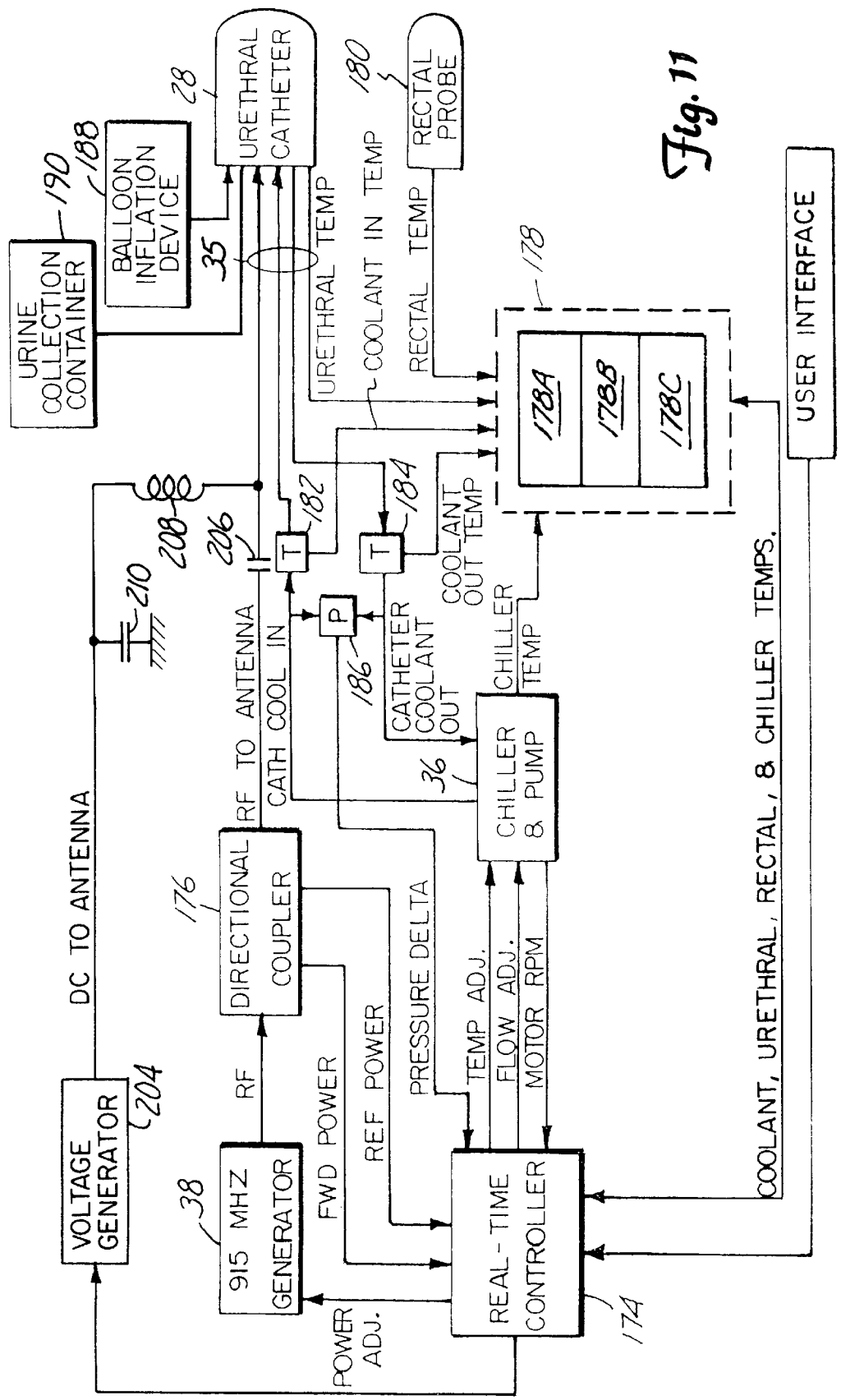
FIG. 11 is a block diagram of the alternative transurethral microwave thermal therapy system of FIG. 10.

FIG. 11 is a block diagram of transurethral microwave thermal therapy system 170. System 170 as shown FIG. 11 is similar to system 170 as shown in FIG. 9, except for the inclusion of variable impedance matching means 200 as described above. FIG. 11 shows the use of reverse biased diode 202 and the components necessary for altering the capacitance of diode 202. Therefore, like components in FIGS. 9 and 11 are identically numbered, and no additional description of the common components is provided.

As seen in FIG. 11, a voltage generator 204 connected to inner conductor 120 of coaxial cable 76 provides a control voltage for altering the capacitance of reverse biased diode 202. The d.c. control signal from voltage generator 204 is superimposed over the microwave power signal applied to coaxial cable 76, such that no additional cables or wires are required. However, voltage generator 204 and microwave generating source 38 must be isolated from each other such that the d.c. signal from voltage generator 204 cannot reach microwave generating source 38, and such that the microwave power signal from microwave generating source 38 cannot reach voltage generator 204.

Voltage generator 204 and microwave generating source 38 are isolated by providing blocking capacitor 206, RF choke 208, and decoupling capacitor 210 as shown in FIG. 11. The d.c. signal from voltage generator 204 sees blocking capacitor 206 and decoupling capacitor 210 as open circuits, while it sees RF choke 208 as a short circuit. The d.c. signal thus cannot travel past blocking capacitor 206 and decoupling capacitor 210, but may travel through RF choke 208. In contrast to the d.c. signal, the microwave power signal sees blocking capacitor 206 and decoupling capacitor 210 as short circuits, while RF choke 208 appears as an open circuit. The microwave power signal thus can travel through blocking capacitor 206 and decoupling capacitor 210, but cannot travel through RF choke 208. The use of blocking capacitor 206, decoupling capacitor 210, and RF choke 208 as shown in FIG. 10 effectively isolates voltage generator 204 from microwave generating source 38, while allowing the direct current and microwave power signal to be superimposed on coaxial cable 76.

As shown in FIG. 11, control and monitoring of microwave generating source 38, cooling system 36, thermometry unit 178, and voltage generator 204 is affected by real time controller (RTC) 174, which is in turn controlled by user interface 172. The operation and control of microwave generating source 38, cooling system 36, and thermometry unit 178 via RTC 174 and user interface 172 is described above in the discussion of FIG. 9. Therefore, no additional discussion of those systems is provided here.

During operation of thermal therapy system 170, the accuracy of the impedance match between antenna 74 and coaxial cable 76 typically changes. As the accuracy of the impedance match changes, the reflected power level from antenna 74 also varies. Increases in the reflected power level indicate that the impedance match between antenna 74 and coaxial cable 76 worsening. RTC 174 continuously monitors the reflected power from antenna 74 (as isolated by directional coupler 176) and adjusts the output of voltage generator 204 to alter the capacitance of reverse biased diode 202 such that an accurate impedance match is obtained and the reflected power is minimized. In this manner, the wide variety of factors which may affect the impedance match between antenna 74 and coaxial cable 76 may be accounted for in real time, and antenna 74 may be continuously "tuned" to match the impedance of antenna 74 to coaxial cable 76.

Although the present invention has been described with reference to preferred embodiments, workers skilled in the art will recognize that changes may be made in form and detail without departing from the spirit and scope of the invention. For example, while the beneficial uses of the microwave antenna-containing catheter of the present invention have been described with respect to the urethra, other intracavitary applications are implied. Similarly, while the use of a reverse-biased diode for providing a voltage-dependant impedance match has been described, other variable impedance matching means which provide a controllable variable reactance can be used in accordance with the present invention. Alternatively, rather than providing a controllable variable reactance, the inductance of the antenna can be altered to match a predetermined reactance. For example, a controllable PIN switching diode may be used to switch out or short a turn or fraction of a turn of the antenna. In this manner, the inductance of the antenna may be changed to match a predetermined reactance. The use of a PIN switching diode to switch out or short a turn or fraction of a turn of the antenna also allows the radiation length of the antenna to be changed.

What is claimed is:

1. A method for treating benign prostatic hyperplasia comprising:

inserting a microwave antenna-containing catheter shaft into a urethra so as to position the microwave antenna adjacent a prostatic region of the urethra, the antenna connected to a variable impedance device;

providing a drive signal to the antenna to apply a radio frequency emission to tissue surrounding the urethra, the radio frequency emission causing molecular excitation of tissue surrounding the urethra sufficient to heat the tissue; and adjusting the variable impedance device, while providing the drive signal, as a function of a reflected power component of the antenna.

2. The method of claim 1, wherein the step of adjusting the variable impedance device is performed continuously.

3. A method for treating tissues with an application of thermal energy comprising:

inserting a microwave antenna-containing catheter into a body cavity so as to position the microwave antenna adjacent a region of tissue to be heated, the antenna including a controllable variable voltage dependent capacitance having a reactive impedance for canceling a reactive component of the impedance of the antenna;

providing a driving signal to the antenna to cause heating of tissue surrounding the catheter;

providing a control voltage to the voltage dependent capacitance as a function of a reflected power component from the antenna.

4. A method for treating tissues with an application of thermal energy comprising:

inserting a microwave antenna-containing catheter into a body cavity so as to position the microwave antenna adjacent a region of tissue to be heated, the antenna being connected to a variable impedance device;

providing a driving signal to the antenna to cause heating of tissue surrounding the catheter; and adjusting the variable impedance device, while providing the driving signal, as a function of a reflected power component from the antenna.

5. The method of claim 4, further comprising measuring forward power delivered to the microwave antenna and reflected power reflected from the microwave antenna, wherein the step of adjusting the variable impedance device as a function of the reflected power component from the antenna comprises minimizing a ratio of measured reflected power to measured forward power.

6. The method of claim 5, wherein the body cavity is a urethra and the region of tissue to be heated surrounding the catheter is prostatic tissue surrounding the urethra, for treating benign prostatic hyperplasia.

7. The method of claim 5, wherein the variable impedance device comprises a controllable variable voltage dependent capacitance having a reactive impedance for canceling a reactive component of an impedance of the antenna, and wherein the step of adjusting the variable impedance device comprises providing a control voltage to the voltage dependent capacitance to minimize the ratio of measured reflected power to measured forward power.

8. The method of claim 5, wherein the step of adjusting the variable impedance device is performed continuously.

* * * * *